United States Patent [19]
Bushick et al.

[11] 3,959,336
[45] May 25, 1976

[54] AMMOXIDATION PROCESS

[75] Inventors: Ronald D. Bushick, Glen Mills; Howard P. Angstadt, Media, both of Pa.

[73] Assignee: Sun Ventures, Inc., Philadelphia, Pa.

[22] Filed: Apr. 15, 1975

[21] Appl. No.: 568,356

Related U.S. Application Data

[63] Continuation-in-part of Ser. No. 404,964, Oct. 10, 1973, abandoned, and a continuation-in-part of Ser. No. 504,939, Sept. 11, 1974, abandoned.

[52] U.S. Cl. .......................... 260/465 C; 252/464; 252/476
[51] Int. Cl.² ..................................... C07C 120/14
[58] Field of Search ............................. 260/465 C

[56] References Cited
FOREIGN PATENTS OR APPLICATIONS
41-16511   9/1966   Japan

*Primary Examiner*—Lewis Gotts
*Assistant Examiner*—Dolph H. Torrence
*Attorney, Agent, or Firm*—J. Edward Hess; Donald R. Johnson; Paul Lipsitz

[57] ABSTRACT

An ammoxidation process for the preparation of nitriles by reaction of m- or p-xylene with ammonia and oxygen using as catalyst an α-alumina supported vanadium-alkali metal bronze promoted with niobium, whereby a high proportion of dinitrile product is obtained. The invention also embodies the niobium promoted catalyst.

16 Claims, No Drawings

AMMOXIDATION PROCESS

BACKGROUND OF THE INVENTION

This is a continuation-in-part of application Ser. No. 404,964 filed Oct. 10, 1973, now abandoned, and a continuation-in-part of application Ser. No. 504,939 filed Sept. 11, 1974 now also abandoned.

Ammoxidation processes are well known in the art and numerous processes with and without added oxygen and with numerous catalysts are described in various U.S. and foreign patents and publications. In those processes using added oxygen, several serious problems have hindered commercial development. One of the major problems where a dinitrile is desired (e.g., terephthalonitrile) is that the by-product mono-nitrile is present in high proportion and this mono-nitrile is recycled for further reaction to dinitrile. The more mononitrile that must be recycled, the larger the equipment that is required and thus it is desirable to have a process where the major proportion of nitriles formed is dinitrile.

The use of vanadium oxides as catalysts in ammoxidation processes is well known. While less common, niobium oxides have also been reported for use in certain ammoxidation procedures. For example, Japanese Pat. No. 43-7610 discloses that unsupported catalysts consisting of mixtures of niobium oxide with tin or titanium oxides are useful for ammoxidation of alkyl-substituted aromatic hydrocarbons to nitriles. U.S. Pat. No. 3,338,952 (Callahan et al., assigned to Standard Oil Co. of Ohio, issued Aug. 29, 1967 Class 260-465.3) discloses an antimony oxide-iron oxide base catalyst used for ammoxidation of aliphatic olefins to nitriles which is promoted with any of a long list of metal oxides including niobium.

It has now been found that an ammoxidation process which gives high dinitrile yields is achieved by catalytically reacting xylene, preferably m- or p-xylene, with ammonia and oxygen using as catalyst an α-alumina-supported vanadiumalkali metal bronze promoted with a niobium oxide. The invention also embodies the novel catalyst composition.

The process of the invention is preferably carried out in a fixed bed mode of operation at a temperature between about 375°C. and 500°C., preferably 400°C. to 450°C., most preferably about 425°C. to 435°C. The source of oxygen is preferably air, but any oxygen source is suitable. The amount of oxygen used in the process may vary over wide limits, but the process enables rather limited amounts of oxygen to be used and this, in turn, is favorable in that less burn of hydrocarbon reactant occurs. Thus, the ratio of oxygen to xylene hydrocarbon in the reactant stream will usually be up to about 6:1, although it is preferable to use no more than about 3:1, preferably 2.5:1 to 3:1, although about 2.0:1 is also quite useful. Likewise the ratio of ammonia to hydrocarbon used in the process of the invention will be preferably about 3:1, or or less, most preferably 2.0:1 to 3:1 although higher ratios, up to 6:1 are also us ul. It is also to be understood that the volume percent concentration of reactants in the feed may be quite high as compared to most ammoxidation procedures and the feed may comprise in percent by volume 3% to 10% xylene, 10% to 20% oxygen, and 7% to 25% ammonia. In the preferred method, the volume percent concentration of reactants corresponding to the above preferred ratios will comprise in percent by volume from about 6 to about 7% p-xylene, from about 11 to about 18% oxygen, and from about 10 to about 22% ammonia. The fact that the process of this invention makes possible this high concentration of reactants is significant in contributing to a very efficient overall process.

As indicated both meta-and-para-xylene are useful reactants for the process. When using m-xylene to obtain isophthalonitrile, however, it is preferred to employ temperatures at the lower end of the range given above and this is in accord with art knowledge that m-xylene is more sensitive to carbon oxide formation than is the p-isomer.

It will be understood that the contact time for the reactants over the catalyst will vary over a wide range, but will usually be from about 0.1 to 20 seconds. The contact time actually used will depend upon catalyst loading, catalyst volume, temperature and other parameters and the skilled art worker will have no difficulty in selecting an appropriate contact time dependent upon these reaction parameters.

The reactant feed stream will, of course, contain other materials, as for example, the inert ingredients of air, recycled toluonitrile, and possibly some small amounts of other by-products associated with the recycle stream. This use of a recycle stream will make possible a still more efficient process.

In addition to the above required parameters of the process it is essential that a particular type of material be used as catalyst. It is known in the art that the addition of an akali metal compound to vanadium pentoxide will, when the mixture is heated yield complex materials with anomalous valencies known as a vanadium bronzes. Such lithium bronzes are discussed by Volkov et al., Zh. Neorg. Khim: 17 (6): 1529–1532 (1972). Vanadium bronzes with sodium are described by Pouchard et al, Bull de la Soc. Chimique de France, No. 7, pages 2742–45 (1968), and No. 11 pages 4343–4348 (1967). Similarly, potassium containing vanadium bronzes are discussed by Holtzberg et al., J. Am. Chem. Soc. Vol. 78, pages 1536–40 (1956). Lithium bronzes are described by Hardy et al., Bull de la Soc. Chimique de France, No. 4, 1056–65 (1965) and by Reisman et al Jour. Physical Chemistry 66 1181–85 (1962). Also of interest is the article by P. Hagenmuller entitled "Tungsten Bronzes, Comprehensive Inorganic Chemistry", edited by J. C. Bailar, Jr. et al. and published in 1973 by Pergamon Press.

All of the above references as well as the references which follow are hereby incorporated herein to teach the chemistry and preparation of the bronzes which are used in this invention.

These bronze materials are prepared by mixing an appropriate alkali metal compound (e.g., carbonate, oxalate, etc.) with vanadium pentoxide and heating the mixture at an elevated temperature for several hours. Depending upon the amount of alkali metal ion added certain phases will be established in accordance with the particular phase diagram pertinent to the mixture. Thus, for example, the Holtzberg et al article referred to above describes the potassium bronze system and the sodium system is shown in the article by Slobodin et al., J. Appl. Chem, (USSR) Vol. 38, pp 799–803 (April 1965). Of the above alkali metal vanadium bronzes, all of which may be used in the process of the invention, the preferred bronzes for use as catalysts are the sodium bronzes and mixtures of the various species also may be employed. Preferred species include Bronze I (BZ I) which has an atomic ratio of sodium to vanadium of 0.167, Bronze II (BZ II) where the atomic ratio is 0.417, and an alpha prime phase ($\alpha'$-phase) where the atomic ratio is 0.50. The terms Bronze I and Bronze II are used herein because these compounds correspond to the compounds called "first BRONZE" and "second BRONZE" by Slobovin and Fotiev, Jour. Applied Chemistry (USSR) 38 Vol. 4 pg. 799 April 1965 where the first bronze is characterized by having 14.3 mole percent of $Na_2O$ in its composition (as does BZ I) and the second bronze has 29.4 mole percent of $Na_2O$ (as does BZ II). These preferred Bronze I and $\alpha'$-phase bronzes may be further characterized by the generic empirical formula $Na_xV_2O_5$ where $x$ is greater than zero and equal to or less than 1. Other bronze systems of the $Na_x V_2O_5$ species are known where x is greater than 1 and these are useful in the process, but are somewhat unstable and therefore not preferred. The BZ I species may be considered as $Na_2O.V_2O_4.5V_2O_5$ or $Na_{0.33}V_2O_5$ which is shown together with related members of the series at pages 573 to 575 of the Hagenmuller article as $\beta$-$Na_xV_2O_5$ where x varies from 0.22 to 0.40, the "$\beta$" designation indicating the particular crystal phase structure of the compound. The BZ II species may be considered as $5Na_2O.V_2O_4.11V_2O_5$ or as $Na_{1+x}V_3O_8$ ($x = 0.25$) which is isotypic with $Li_{1+x}V_3O_8$ and is shown at page 584 of the Hagenmuller article mentioned above. The $\alpha'$-phase is characterized as $Na_xV_2O_5$ where $x = 0.7$ to 1.0 (see page 577 of the Hagenmuller article). Also characteristic of the bronzes are their x-ray diffraction patterns wherein the strongest lines are as follows:

BZ I: 9.6, 7.3, 4.75, 3.87, 3.47, 3.38, 3.21, 3.11, 3.08, 2.92, 2.90, 2.727, 2.55, 2.45, 2.38, 2.18, 1.97, 1.87, 2.803, 1.74, 1.535, 1.492.

BZ II: 6.9, 7.04, 5.81, 3.87, 3.62, 3.50, 3.45, 3.21, 3.10, 3.01, 3.67, 2.57, 2.43, 2.32, 2.27, 2.02, 1.97, 1.96, 1.81, 1.72, 1.86, 1.504, 1.333, 1.39.

$\alpha'$: 11.3, 5.645, 4.82, 4.436, 3.667, 3.456, 2,967, 2.889, 2.882, 2.799, 2.604, 2.436, 2.412, 2.291, 2.0196, 1.889, 1.803, 1.77, 1.689, 1.635, 1.592, 1.479.

The $\alpha'$-prime phase as with the other bronzes may be obtained by the methods described in the literature and placed on the support for use in the process, or it may be made in situ. This is readily achieved by treating the BZ II on the support with a reducing atmosphere (e.g., ammonia) or a stream similar to the hydrocarbon, ammonia and oxygen; e.g., an oxygen to hydrocarbon mole ratio of less than about 3.0.

As indicated the catalyst bronzes may comprise a mixture of the above discussed bronzes and preferred catalysts will comprise a mixture predominant in either BZ II or the $\alpha$-prime phase or both. While BZ I used above is operable, it is preferred in order to keep the carbon oxides to a minimum to avoid having a predominant amount of BZ I in the catalyst composition.

In order to obtain the niobium-promoted catalyst used in the invention, the appropriate niobium compound is simply added during the catalyst preparation. In one technique $Nb_2O_5$ is added to all of the powdered catalyst ingredients and physically mixed and the mixture pressed into pellets for use. In another technique, a water soluble niobium salt (e.g., potassium niobate) is added and used with the other catalyst ingredients to impregnate the support. The amount of niobium loading on the total catalyst will be from about 0.25% to about 10% by weight (as $Nb_2O_5$), but from about 0.2 to about 2% is preferred.

The catalyst support used in the process of the invention will be comprised of $\alpha$-alumina. $\alpha$-alumina is well known in the art and is exemplified by natural corundum and by a synthetic varieties which are commercially available. These materials have a high density (on the order of about 0.75 to 1.0 gm/cc.) and very low surface area (on the order of $6m^2/gm$ or less). Generally the $\alpha$-alumina will contain enough sodium ions so that the sodium bronzes may be made without any addition of sodium or other alkali metal compounds. But if insufficient sodium is present, enough may be added to give the desired bronze. In making the supported catalyst all that is required is to make an aqueous slurry of powdered (170 mesh or finer) $\alpha$-alumina, alkali metal salt (preferably carbonate) and $V_2O_5$, evaporate off the water, pelletize and calcine the pellets at about 500°–600°C. for several hours, while passing a slow flow of air through the furnace. Alternatively, and preferably, the catalyst may be placed on the support by an impregnation technique where and aqueous vanadium oxalate solution containing the appropriate amount of alkali metal is deposited onto the $\alpha$-alumina support, which method is well known in the art.

As pointed out above, in making the catalyst alkali metal ions (usually in the form of the carbonate) are added to ensure that a bronze is formed. In a particularly preferred catalyst system where a sodium-vanadium bronze is desired, the amount of sodium ion employed to make the catalyst will be at a ratio of sodium to vanadium of 0.30 and such catalyst appears to be of high bronze purity devoid of extraneous materials which migh degrade catalyst performance.

As indicated, the catalyst support will be comprised of $\alpha$-alumina but may contain other components such as silica and other metal oxides as well as the normal contaminants found in $\alpha$-alumina; e.g., iron, magnesium, and the like. However, at least about 75% by weight of the support will be $\alpha$-alumina.

The amount of catalyst on the support (e.g., catalyst loading) will be from about 1 to 20% by weight, preferably about 3 to 8%. The surface area of the catalysts used in the process is generally quite low being less than $10m^2/gm$ and usually 1 to $5m^2/gm$. Pore volume of the catalyst is such that the major proportion of the pores have diameters less than about 1 micron, being on the order of about 0.2 to 1.0 micron.

After a niobium-promoted BZ I or a promoted mixed BZ I and BZ II catalyst is prepared, but before its use, it is preferred to age the catalyst by a heat treatment at about 500°C. to about 750°C. for 3 to 4 hours. This treatment will convert most, if not all, of the BZ I to BZ II which is preferred over BZ I.

The catalyst composition of the invention is thus an alkali metal vanadium bronze promoted with niobium and is preferably a promoted Bronze II or $\alpha$-prime phase. The catalysts are preferably pelletized for use, but may also be employed in powder form.

The ammoxidation is carried out preferably in conventional apparatus, the reaction gases passing over the catalyst at reaction temperature and the effluent gases separated into the appropriate product and by-product streams. Particular advantages of the process of the invention reside in (a) low formation of carbon oxides, (b) high selectivity for formation of dinitriles, (c) low oxygen and ammonia to hydrocarbon ratios, (d) dealkylation of polyalkyl aromatics is minimized (i.e., benzonitrile is formed in only small amounts) and (e) the process temperature is rather low. In order to further describe and illustrate the invention the following examples are given:

PREPARATION OF CATALYSTS

Method A

The α-alumina support is ground into a fine powder having a particle size of about 170 mesh or less and the appropriate amount of $Nb_2O_5$ and $V_2O_5$ added to it. If analysis shows that the amount of alkali metal in the α-alumina is insufficient the desired amount sodium carbonate or other alkali metal salt is added. The mixture is then ground dry and then water is added and the mixture further agitated to make a slurry; the slurry is poured into an evaporating dish and evaporated to dryness. The dry residue is mixed further to break up agglomerates and water added to make a past which is formed into pellets are then calcined at 540°C. for about 4 hours while air at the rate of 2.5 l/min is passed through the furnace. After cooling the catalyst pellets are ready for use.

Method B

Granulated alumina (8 – 16 mesh) is heated at 1300°C. for 4 hours. Potassium niobate ($4K_2O.3Nb_2O_5.16H_2O$) and vanadium pentoxide are suspended in 5 parts of water, heated to 80°C., and oxalic acid is added slowly to obtain a blue-colored vanadium oxalate solution. Sodium carbonate is added and the alumina is also placed in the solution. The mixture is dried over a water bath with agitation. While air is pumped in, it is indurated in a furnace at 400°C. for 16 hours to obtain the catalyst ready for use after cooling.

Experimental Procedures

An appropriate quantity of catalyst (with or without inert diluent, e.g., quartz) was placed in a fixed bed quartz reactor (1¼ inches in diameter and 24 inches long). Inert packing above the catalyst serves as a preheater section and a small amount (about 1–2 inches) of similar inert packing was placed in the bottom of the reactor to support the catalyst in the reaction zone. The upper end of the reactor was equipped with an assembly having multiple openings through which the hydrocarbons, ammonia, and air (or oxygen-helium or oxygen-nitrogen mixtures) can be metered. The reactants can be mixed in this "mixing chamber" or premixed and then fed into the reactor which was operated at essentially atmospheric pressure. The rate of gas flow was adjusted so as to produce the desired contact time at a given reaction temperature over a given volume of catalyst.

The effluent gases were passed from the reactor into a chilled flask where the products were collected along with ammonium carbonate and water. The remaining escaping gas was passed through a cold water cooled condenser, a drying tube, an ascarite tube, and finally captured in large polyvinylchloride bag.

The analysis of the organic layer, water layer, gas sample from the bag, and the weight increase of the ascarite tube (due to $CO_2$ not bound up as ammonium carbonate) enables calculation of the results (i.e., conversion, carbon balance, yield, etc.).

Examples 1–4

Using the above described procedure a catalyst of a sodium-vanadium bronze on α-alumina containing 8.5% vanadium (as $V_2O_5$) and 0.6% $Nb_2O_5$ was prepared. Operating the ammoxidation process at 430°C., the data shown in Table I was obtained.

TABLE I

| Ex. No. | Mole Ratio $NH_3/HC$ | Mole Ratio $O_2HC$ | Ammoxidation of p-Xylene Contact Time (sec.) | Yield (Mole Per Cent) CO | $CO_2$ | BN* | TN* | TPN* | C. Bal. | % Conv. |
|---|---|---|---|---|---|---|---|---|---|---|
| 1 | 3.2 | 3.0 | 2.8 | 1.7 | 7.5 | 0.6 | 25.2 | 65.0 | 74.5 | 86.7 |
| 2 | 3.2 | 3.0 | 1.9 | 0.0 | 5.1 | 0.6 | 33.3 | 61.0 | 101.8 | 39.2 |
| 3 | 3.2 | 6.0 | 2.8 | 2.1 | 16.9 | 0.2 | 8.3 | 72.5 | 93.6 | 98.9 |
| 4 | 3.2 | 4.0 | 6.8 | 0.0 | 9.2 | 3.2 | 29.7 | 57.9 | 88.7 | 85.2 |

*BN = Benzonitrile
TN = Toluonitrile
TPN = Terephthalonitrile

Examples 5 to 9

Ammoxidation was carried out as described using a mole ratio of ammonia to p-xylene of 2.3:1 with the other reaction parameters shown in Table II.

As can be seen from the data, the niobium promoted catalyst of the invention gives results favorable in denitrile specificity.

Example 10

In carrying out the process of Examples 5 to 9 with m-xylene, but at 400°C., the same high specificity to isophthalonitrile is achieved.

Although the above examples illustrate the process of the invention with a fixed bed system it will be understood that the process is equally useful with other systems such as a fluidized bed, a moving bed, and the like. Thus, for example, a suitably high yield of total nitriles (e.g., toluonitrile and terephthalonitrile) is obtained from p-xylene with a fluidized bed system using a stainless steel tube 1.25 inches in diameter and 6 feet long operating under the following parameters:

Catalyst: Bronze II on α-alumina-niobium promoted
800 g. catalyst in tube
Expanded bed height 2' to 4'
Reaction Conditions: 400°C.
$O_2$p-xylene = 2.5
$NH_3$p-xylene = 2.5
Contact time = 6 sec.
Pressure = 1 atmosphere When carrying out the process in a fixed bed mode the pressure of the system will be preferably essentially atmospheric as conversions and selectivity in the conventional fixed bed drop off at higher pressures due to hot spotting. To avoid such problems it is preferable to employ a fluidized bed system which overcomes the hot spotting and lends itself to very efficient operation at higher pressures. Fluidized bed operations will be carried out preferably at from about 1 to about 5 atmospheres.

TABLE II

| Ex. No. | Mole Ratio O₂/HC | Temp. °C. | C.T. (sec) | Ammoxidation of p-Xylene Yield (Mole Per Cent) | | | | | C. Bal. | % Conv. |
| --- | --- | --- | --- | --- | --- | --- | --- | --- | --- | --- |
| | | | | CO | CO₂ | BN | TN | TPN | TN + TPN | | |
| 5 | 4.4 | 430 | 2.9 | 4.8 | 11.8 | 0.3 | 19.1 | 63.9 | 83.0 | 91.4 | 92.8 |
| 6 | 3.0 | 450 | 3.0 | 1.0 | 11.6 | 1.3 | 18.9 | 67.2 | 86.1 | 88.0 | 88.0 |
| 7 | 4.0 | 440 | 2.9 | 2.5 | 9.3 | 0.9 | 22.8 | 54.5 | 87.3 | 82.2 | 86.8 |
| 8 | 3.5 | 440 | 2.9 | 2.9 | 11.2 | 0.7 | 17.5 | 67.7 | 85.2 | 89.6 | 87.7 |
| 9 | 3.7 | 430 | 1.9 | 0.8 | 8.9 | 0.0 | 36.7 | 53.7 | 90.4 | 70.0 | 83.0 |

Catalyst: A sodium vanadium Bronze II on α-alumina containing 15% $V_2O_5$ and 0.6% $Nb_2O_5$

The invention claimed is:

1. In the ammoxidation process of m- or p-xylene to the corresponding nitriles, which process is carried out by reacting said xylene with ammonia and oxygen at about 375°C. to about 500°C., the improvement of using as catalyst an alkali metal vanadium bronze supported on α-alumina and promoted with about 0.25% to about 10% by weight of $Nb_2O_5$.

2. An ammoxidation process for preparing nitriles from m- and p-xylene which comprises reacting said xylene and ammonia at a temperature of from about 375°C. to about 500°C. in the presence of added oxygen, the molar ratio of ammonia to xylene being from about 2.0:1 to about 6:1, the volume percent concentration of the reactant feed being about 3% to 10% xylene, 7% to 25% ammonia, and 10% to 20% oxygen, and the catalyst for said reaction comprising at least about 1 to 10% by weight of an alkali metal vanadium bronze supported on α-alumina and promoted with about 0.25% to about 10% by weight of $Nb_2O_5$.

3. An ammoxidation process for preparing terephthalonitrile from p-xylene which comprises reacting p-xylene and ammonia at a temperature of from about 400°C. to about 450°C. in the presence of added oxygen, the molar ratio of oxygen to xylene being from about 2:1 to about 3:1, the volume percent concentration of the reactant feed being about 3% to 10% xylene, 7% to 25% ammonia, and 10% to 20% oxygen, and the catalyst for said reaction comprising at least about 1 to 10% by weight of an alkali metal vanadium bronze supported on α-alumina and promoted with about 0.2% to about 2% by weight of $Nb_2O_5$.

4. The process of claim 3 where the catalyst is a sodium vanadium bronze.

5. The process of claim 4 where the catalyst is predominantly BZ II or the α-prime phase.

6. The process of claim 3 operated in a fixed bed mode at essentially atmospheric pressure where the temperature is from about 400°C. to about 435°C., the ratio of oxygen to xylene and of ammonia to xylene is from about 2.0:1 to about 3.0:1, and concentration of feed is about 6 to about 7% xylene, about 10% to about 22% ammonia and about 11% to about 18% oxygen, and the catalyst is a sodium vanadium bronze.

7. The process of claim 6 where the catalyst is predominantly BZ II.

8. The process of claim 6 where the catalyst is predominantly the α-prime phase.

9. The process of claim 6 where the catalyst is a mixture of BZ II and the α-prime phase.

10. The process of claim 3 operated in a fluidized bed mode at 1 to about 5 atmospheres where the temperature is from about 400°C. to about 435°C., the ratio of oxygen to xylene and of ammonia to xylene is from about 2.0:1 to about 3.0:1, the concentration of feed is about 6% to about 7% xylene, about 10% to about 22% ammonia and about 11% to about 18% oxygen, and the catalyst is a sodium vanadium bronze.

11. The process of claim 10 where the catalyst is predominantly BZ II.

12. The process of claim 11 where the catalyst is predominantly the α-prime phase.

13. The process of claim 11 where the catalyst is a mixture of BZ II and the α-prime phase.

14. The process of claim 6 where the xylene is m-xylene and the reaction temperature is from about 375°C. to about 425°C.

15. The process of claim 2 operated in a fixed bed where the xylene is meta-xylene and the reaction temperature is from about 375°C. to about 425°C.

16. The process of claim 2 operated in a fluidized bed where the xylene is m-xylene and the reaction temperature is from about 375°C. to about 425°C.

* * * * *